United States Patent [19]

Nomura et al.

[11] Patent Number: 4,954,612

[45] Date of Patent: Sep. 4, 1990

[54] SOLVENT-SOLUBLE POLYIMIDE AND PRODUCTION THEREOF

[75] Inventors: Yoshihiro Nomura; Kazuhito Hanabusa; Hiroshi Minamisawa, all of Ichihara; Takashi Morinaga, Chiba; Toichi Sakata, Katsuta; Yoshiyuki Mukoyama, Hitachi; Hiroshi Nishizawa, Kitaibaraki; Hiromu Miyajima, Ichihara, all of Japan

[73] Assignee: Hitachi Chemical Co., Ltd., Tokyo, Japan

[21] Appl. No.: 309,878

[22] Filed: Feb. 14, 1989

[30] Foreign Application Priority Data

Feb. 15, 1988 [JP] Japan .................................. 63-32360

[51] Int. Cl.⁵ ...................... C08G 69/12; C08G 69/26; C08G 75/00; C08G 79/02

[52] U.S. Cl. .................................. 528/353; 528/125; 528/126; 528/128; 528/172; 528/185; 528/188; 528/189; 528/208; 528/220; 528/229; 528/352

[58] Field of Search ............... 528/353, 125, 126, 128, 528/172, 185, 188, 189, 208, 220, 229, 352

[56] References Cited

U.S. PATENT DOCUMENTS 4,588,804  5/1986  Fryd ..................................... 428/125
4,696,994  9/1987  Nakajima et al. ................... 528/176

Primary Examiner—John Kight, III
Assistant Examiner—P. Hampton-Hightower
Attorney, Agent, or Firm—Antonelli, Terry, Stout & Kraus

[57] ABSTRACT

A solvent-soluble polyimide obtained from an exo-form dicarboxylic acid anhydride with an aromatic diamine, e.g. 2,2,-bis[4-(4-aminophenoxy)phenyl]propane is improved in film-forming properties and transparency, and particularly suitable for producing an orientation controlling film in a liquid crystal display device.

13 Claims, 7 Drawing Sheets

SOLVENT-SOLUBLE POLYIMIDE AND PRODUCTION THEREOF

BACKGROUND OF THE INVENTION

This invention relates to a solvent-soluble polyimide and a process for producing the same.

It is known that aromatic polyimides excellent in heat resistance can be obtained by polycondensation of aromatic tetracarboxylic acid anhydrides or derivatives thereof and aromatic diamines. More in detail, a polyamide-acid is first synthesized, followed by curing at high temperatures for imidization to yield a polyimide. As a typical example, an aromatic polyamide-acid is synthesized from pyromellitic anhydride and diaminodiphenyl ether. But such an aromatic polyamide-acid should be cured at such a high temperature as 300° C. or higher for imidization. The thus obtained aromatic polyimide is generally insoluble in a solvent. It is also known that a polyimide can be produced from an alicyclic dibasic acid and a diamine via polyamide-acid (Japanese Patent Unexamined Publication No. 60-135430). But this reference is quite silent on the production of a solvent-soluble polyimide.

On the other hand, it is proposed in Japanese Patent Unexamined Publication No. 59-179623 to produce a solvent-soluble polyimide by properly selecting a special combination of monomers. But according to this method, the resulting aromatic polyimide film is colored in a yellowish brown color and poor in light transmittance. Thus, a polyimide solution having good light transmittance has been desired in fields wherein light curing or light transmittance has an important meaning.

SUMMARY OF THE INVENTION

It is an object of the present invention to provide a solvent-soluble polyimide good in transparency and film forming properties overcoming the problems mentioned above, and a process for producing the same.

The present invention provides a solvent-soluble polyimide obtained by reacting an exo-form dicarboxylic acid anhydride represented by the formula:

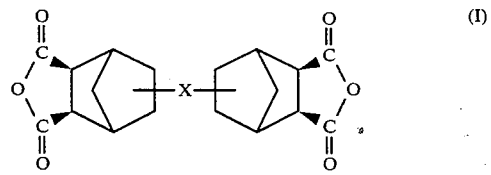

wherein X is S or SO₂, with an aromatic diamine in a polar solvent, followed by dehydration ring closure.

The present invention also provides a process for producing a solvent-soluble polyimide which comprises reacting an exo-form dicarboxylic acid anhydride represented by the formula:

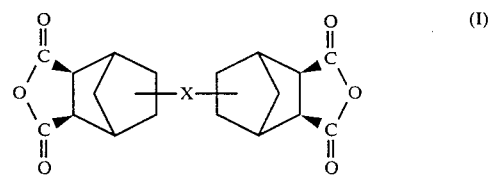

wherein X is S or SO₂, with an aromatic diamine in a polar solvent, followed by dehydration ring closure.

The present invention further provides a process for using said solvent-soluble polyimide as an orientation cotrolling film in a liquid crystal display device.

DESCRIPTION OF THE PREFERRED EMBODIMENTS

Figure 1:
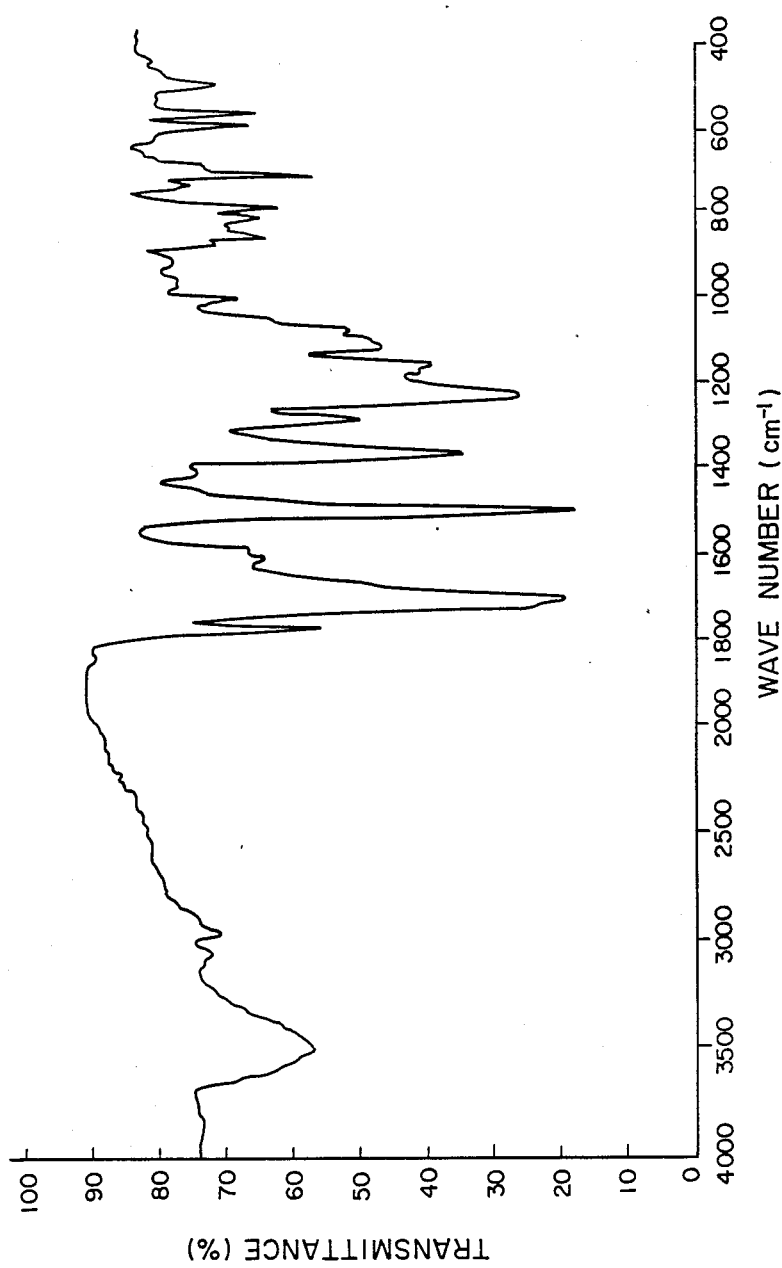
FIG. 1 is an infrared absorption spectrum of polyimide obtained in Example 6.

The solvent-soluble polyimide of the present invention can be obtained by reacting a special exo-form dicarboxylic acid anhydride with an aromatic diamine.

The special exo-form dicarboxylic acid anhydride is represented by the formula:

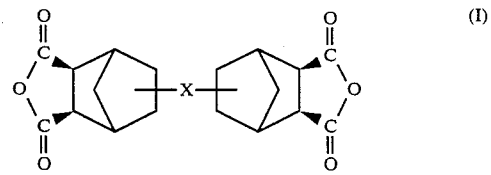

wherein X is S or SO₂. Examples of the compound of the formula (I) are bis(exo-bicyclo[2,2,1]heptane-2,3-dicarboxylic acid anhydride) sulfide (hereinafter referred to as "exo-HAC-S") and bis(exo-bicyclo[2,2,1]heptane-2,3-dicarboxylic acid anhydride) sulfone (hereinafter referred to as "exo-HAC-S02").

Exo-HAC-S can be synthesized by reacting exo-bicyclo[2,2,1]-heptene-(5)-2,3-dicarboxylic acid anhydride with hydrogen sulfide in the presence of a radical initiator.

Exo-HAC-SO₂ can be synthesized by suspending exo-HAC-S in a suitable solvent and reacting it with an oxidizing agent such as hydrogen peroxide (e.g. see Japanese Patent Unexamined Publication No. 48-92354).

In the present invention, a compound of the formula (I) can be used alone as an acid component, or can be used together with one or more other carboxylic acid anhydrides. When benzophenonetetracarboxylic dianhydride is used together as an acid component, it is preferable to use 40 to 80% by mole of the exo-form dicarboxylic acid anhydride of the formula (I) and 60 to 20% by mole of benzophenonetetracarboxylic dianhydride, more preferably 50 to 70% by mole of the former and 50 to 30% by mole of the latter. In this case, so far as benzophenonetetracarboxylic dianhydride is used in the range of 20 to 60% by mole, the obtained polyimide is improved in water absorption and no undesirable gelation or no undesirable deposition of the resin takes place during the imidization of the polyamide-acid in a solution.

The use of the compound of the formula (I) is essential in the present invention. But so far as alicyclic polyimides having a certain molecular weight in terms of reduced viscosity of 0.3 dl/g or more measured in a polar solvent can be obtained, one or more modifying agents can be added to the compound of the formula (I). As the modifying agent, there can be used acid dianydrides such as bis(endo-bicyclo[2,2,1]heptane-2,3-dicarboxylic acid anhydride) sulfide (hereinafter referred to as "endo-HAC-S"), bis(endobicyclo[2,2,1]heptane-2,3-dicarboxylic acid anhydride) sulfone (hereinafter referred to as "endo-HAC-$SO_2$"), pyromellitic dianydride, benzophenonetetracarboxylic dianhydride, etc.

These modifying agents can be used in an amount of preferably 50% by mole or less, more preferably 30% by mole or less based on the total amounts of dicarboxylic acid anhydrides. In order to maintain transparency of polyimides obtained, it is better to use the modifying agent in a smaller amount.

As the aromatic diamine, there can be used the following compounds:

Compounds represented by the formula:

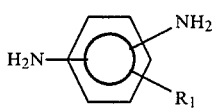

wherein $R_1$ is a hydrogen atom, a lower alkyl group preferably having 1 to 6 carbon atoms, a lower alkoxy group preferably having 1 to 6 carbon atoms, a chlorine atom or a bromide atom.

Compounds represented by the formula:

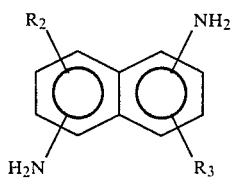

wherein $R_2$ and $R_3$ are independently a hydrogen atom, a lower alkyl group preferably having 1 to 6 carbon atoms, a lower alkoxy group preferably having 1 to 6 carbon atoms, a chlorine atom or a bromine atom.

Compounds represented by the formula:

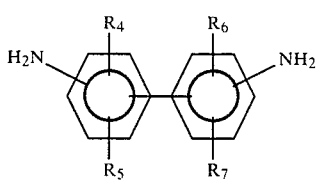

wherein $R_4$, $R_5$, $R_6$ and $R_7$ are independently a hydrogen atom, a lower alkyl group preferably having 1 to 6 carbon atoms, a lower alkoxy group preferably having 1 to 6 carbon atoms, a chlorine atom or a bromine atom.

Compounds represented by the formula:

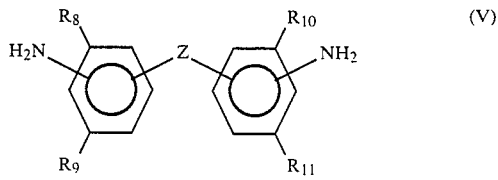

wherein Z is an alkylene group having 1 to 6 carbon atoms,

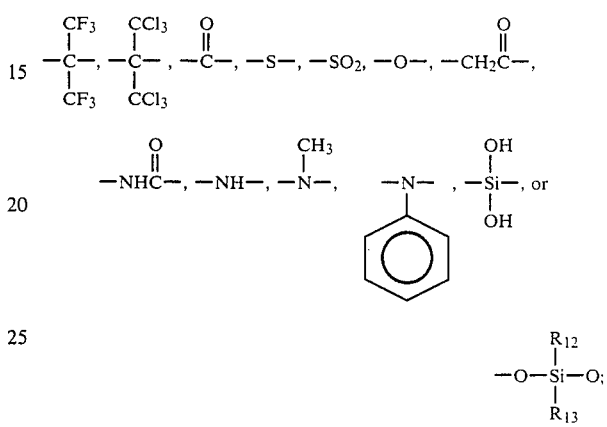

$R_8$, $R_9$, $R_{10}$ and $R_{11}$ are independently a hydrogen atom, a lower alkyl group preferably having 1 to 6 carbon atoms, a lower alkoxy group preferably having 1 to 6 carbon atoms, a chlorine atom, or a bromine atom; and $R_{12}$ and $R_{13}$ are independently a lower alkyl group preferably having 1 to 6 carbon atoms.

Compounds represented by the formula:

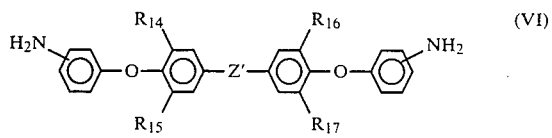

wherein Z' is an alkylene group having 1 to 6 carbon atoms,

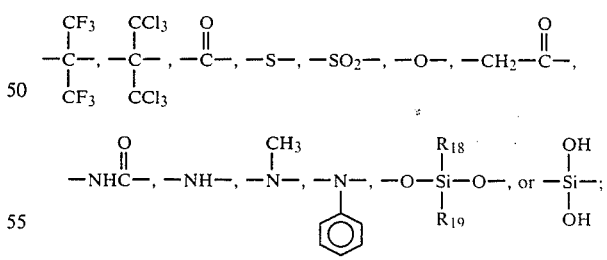

$R_{14}$, $R_{15}$, alkyl group preferably having 1 to 6 carbon atoms, a lower alkoxy group preferably having 1 to 6 carbon atoms, a chlorine atom or a bromine atom; and $R_{18}$ and $R_{19}$ are independently a lower alkyl group preferably having 1 to 6 carbon atoms.

Concrete examples of the compounds of the formulae (II) to (VI) are as follows:
2,2-bis[4-(4-aminophenoxy)phenyl]propane,
2,2-bis[3-methyl-4-(4-aminophenoxy)phenyl]propane,
2,2-bis[3-chloro-4-(4-amino-phenoxy)phenyl]propane,
2,2-bis[3-bromo-4-(4-aminophenoxy)phenyl]propane, 2,2-bis[3-ethyl-4-(4-aminophenoxy)phenyl]propane,
2,2-bis[3-propyl-4-(4-aminophenoxy)phenyl]propane,
2,2-bis[3-isopropyl-4-(4-aminophenoxy)phenyl]propane,
2,2-bis[3-butyl-4-(4-aminophenoxy)phenyl]propane,
2,2-bis[3-sec-butyl-4-(4-aminophenoxy)phenyl]propane,
2,2-bis[3-methoxy-4-(4-aminophenoxy)phenyl]propane,
2,2-bis[3-ethoxy-4-(4-aminophenoxy)phenyl]propane,
2,2-bis[3,5-dimethyl-4-(4-aminophenoxy)phenyl]propane,
2,2-bis[3,5-dichloro-4-(4-aminophenoxy)phenyl]propane,
2,2-bis[3,5-dibromo-4-(4-aminophenoxy)phenyl]propane,
2,2-bis[3,5-dimethoxy-4-(4-aminophenoxy)phenyl]propane,
2,2-bis[3-chloro-4-(4-aminophenoxy)-5-methylphenyl]propane,
1,1-bis[4-(4-aminophenoxy)phenyl]ethane,
1,1-bis[3-methyl-4-(4-aminophenoxy)phenyl]ethane,
1,1-bis[3-chloro-4-(4-aminophenoxy)phenyl]ethane,
1,1-bis[3-bromo-4-(4-aminophenoxy)phenyl]ethane,
1,1-bis[3-ethyl-4-(4-aminophenoxy)phenyl]ethane,
1,1-bis[3-propyl-4-(4-aminophenoxy)phenyl]ethane,
1,1-bis[3-isopropyl-4-(4-aminophenoxy)phenyl]ethane,
1,1-bis[3-butyl-4-(4-aminophenoxy)phenyl]ethane,
1,1-bis[3-sec-butyl-4-(4-aminophenoxy)phenyl]ethane,
1,1-bis[3-methoxy-4-(4-aminophenoxy)phenyl]ethane,
1,1-bis[3-ethoxy-4-(4-aminophenoxy)phenyl]ethane,
1,1-bis[3,5-dimethyl-4-(4-aminophenoxy)phenyl]ethane,
1,1-bis[3,5-dichloro-4-(4-aminophenoxy)phenyl]ethane,
1,1-bis[3,5-dibromo-4-(4-aminophenoxy)phenyl]ethane,
1,1-bis[3,5-dimethoxy-4-(4-aminophenoxy)phenyl]ethane,
1,1-bis[3-chloro-4-(4-aminophenoxy)phenyl-5-methylphenyl]ethane,
bis[4-(4-aminophenoxy)phenyl]methane,
bis[3-methyl-4-(4-aminophenoxy)phenyl]methane,
bis[3-chloro-4-(4-aminophenoxy)phenyl]methane,
bis[3-bromo-4-(4-aminophenoxy)phenyl]methane,
bis[3-ethyl-4-(4-aminophenoxy)phenyl]methane,
bis[3-propyl-4-(4-aminophenoxy)phenyl]methane,,
bis[3-isopropyl-4-(4-aminophenoxy)phenyl]methane,
bis[3-butyl-4-(4-aminophenoxy)phenyl]methane,
bis[3-sec-butyl-4-(4-aminophenoxy)phenyl]methane,
bis[3-methoxy-4-(4-aminophenoxy)phenyl]methane,
bis[3-ethoxy-4-(4-aminophenoxy)phenyl]methane,
bis[3,5-dimethyl-4-(4-aminophenoxy)phenyl]methane,
bis[3,5-dichloro-4-(4-aminophenoxy)phenyl]methane,
bis[3,5-dibromo-4-(4-aminophenoxy)phenyl]methane,
bis[3,5-dimethoxy-4-(4-aminophenoxy)phenyl]methane,
bis[3-chloro-4-(4-aminophenoxy)-5-methylphenyl]methane,
1,1,1,3,3,3-hexafluoro-2,2-bis[4-(4-aminophenoxy)phenyl]propane,
1,1,1,3,3,3-hexachloro-2,2-bis[4-(4-aminophenoxy)phenyl]propane,
3,3-bis[4-(4-aminophenoxy)phenyl]pentane,
1,1-bis[4-(4-amino-phenoxy)phenyl]propane,
1,1,1,3,3,3-hexafluoro-2,2-bis[3,5-dimethyl-4-(4-aminophenoxy)phenyl]propane,
1,1,1,3,3,3-hexachloro-2,2-bis[3,5-dimethyl-4-(4-aminophenoxy)phenyl]propane,
3,5-bis[3,5-dimethyl-4-(4-aminophenoxy)phenyl]pentane,
1,1-bis[3,5-dimethyl-4-(4-aminophenoxy)phenyl]propane,
1,1,1,3,3,3-hexafluoro-2,2-bis[3,5-dibromo-4-(4-aminophenoxy)phenyl]propane,
1,1,1,3,3,3-hexachloro-2,2-bis[3,5-dibromo-4-(4-aminophenoxy)phenyl]propane,
3,3-bis[3,5-dibromo-4-(4-aminophenoxy)phenyl]pentane,
1,1,bis[3,5-dibromo-4-(4-aminophenoxy)phenyl]propane,
2,2-bis[4-(4-aminophenoxy)phenyl]butane,
2,2-bis[3-methyl-(4-aminophenoxy)phenyl]butane,
2,2-bis[3,5-dimethyl-4-(4-aminophenoxy)phenyl]butane,
2,2-bis[3,5-dibromo-4-(4-aminophenoxy)phenyl]butane,
1,1,1,3,3,3-hexafluoro-2,2-bis[3-methyl-4-(4-aminophenoxy)phenyl]propane,
m-phynylenediamine,
p-phenylenediamine,
4,4'-diaminodiphenylmethane,
4,4'-diaminodiphenyl ether,
4,4'-diaminodiphenyl sulfone,
4,4'-diaminodiphenylpropane-2,2,4,4'-diaminodiphenyl sulfide,
1,5-diaminonaphthalene,
4,4'-diaminodiphenylethane,
m-toluylenediamine,
p-toluylenediamine,
3,4'-diaminobenzanilide,
1,4-diaminonaphthalene,
3,3'-dichloro-4,4'-diaminodiphenyl,
benzidine,
4,4'-diaminodiphenylamine,
4,4'-diaminodiphenyl-N-methylamine,
4,4'-diaminodiphenyl-N-phenylamine,
3,3'-diaminodiphenyl sulfone,
4,4'-diaminodiphenyldiethylsilane,
4,4,-diaminodiphenylsilane, etc.

As the diamine component, one or more aliphatic diamines and/or alicyclic diamines can be co-used. Examples of the aliphatic diamines and alicyclic diamines are piperazine, hexamethylenediamine, heptamethylenediamine, octamethylenediamine, nonamethylenediamine, decamethylenediamine, p-xylylenediamine, m-xylylenediamine, tetramethylenediamine, dodecamethylenediamine, 4,4-dimethylheptamethylenediamine, 3-methylheptamethylenediamine, 2,11-diaminododecane, 1,12-diaminooctadecane, cyclohexane-1,3-diamine, cyclohexane-1,4-diamine, etc.

When the aliphatic and/or alicyclic diamines are co-used, they are used in amounts of 50% by mole or less based on the total amount of diamine component. Considering reactivity and heat resistance of the resulting polyimide, the amount is preferably 20% by mole or less based on the total amount of diamine component. As a method for copolymerization, there can be employed a method wherein the aliphatic and/or alicyclic diamine is directly copolymerized, or a method wherein the diamine is converted to imidodicarboxylic anhydride with an aromatic tetrabasic acid anhydride, followed by copolymerization.

As the diamine component, it is also possible to use a diaminosiloxane. As the diaminosiloxane, there can be used a compound represented by the formula:

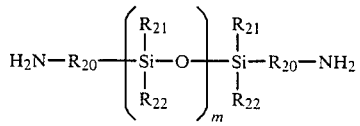
(VII)

wherein $R_{20}$ is a divalent hydrocarbon group such as an alkylene group preferably having 1 to 5 carbon atoms, a phenylene group, a phenylene group substituted with an alkyl group, or the like; $R_{21}$ and $R_{22}$ are independently an alkyl group preferably having 1 to 5 carbon atoms, a phenyl group, a phenyl group substituted with an alkyl group, etc.

Examples of the diaminosiloxane of the formula (VII) are as follows:

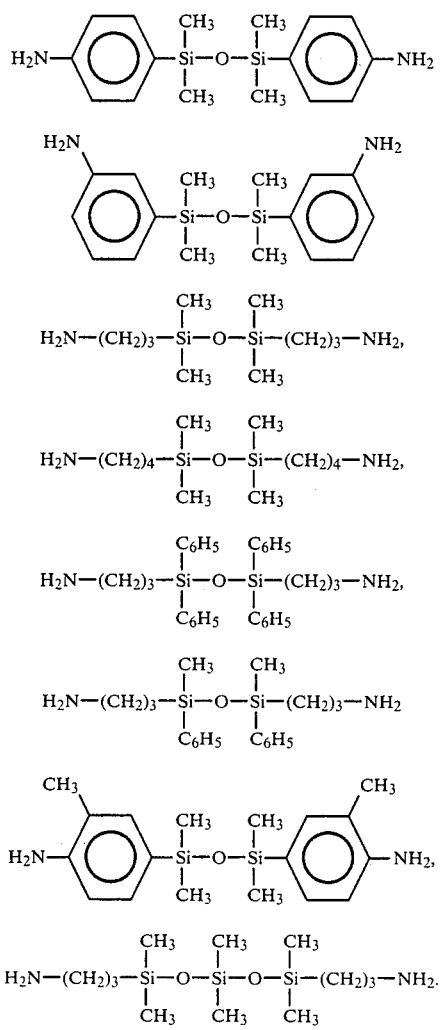

The use of diaminosiloxane is effective for improving heat resistance. Thus, it is preferable to use the diaminosiloxane in an amount of 0.5% by mole or more and 50% by mole or less base on the total amount of the diamine component, considering the reactivity. The use of the diaminosiloxane in an amount of 5 to 25% by mole is particularly preferable from the viewpoint of the reactivity and heat resistance. When the diaminosiloxane is used, it can be copolymerized as it is, or it can be first reacted with an aromatic tetrabasic acid anhydride to form an imidodicarboxylic acid anhydride, which is then polymerized.

The total amount of aliphatic and/or alicyclic diamine and diaminosiloxane in the diamine component is preferably 50% by mole or less, more preferably 30% by mole or less, considering the solubility in a solvent.

In order to obtain the polyimide polymer of the present invention, a dicarboxylic acid anhydride of the formula (I) is reacted with a diamine in an aprotic polar solvent at a temperature preferably from room temperature to 210° C., more preferably 160° to 200° C. Examples of the aprotic polar solvent is dimethylacetamide, dimethyl sulfoxide, N-methylpyrrolidone, hexamethylphosphorictriamide, etc. Since this reaction accompanys a dehydration ring closure, it is convenient to add a dehydrating agent to the reaction system in order to obtain a polyimide having a high molecular weight. Examples of the dehydrating agent is pentavalent phosphoric acid, a combination of acetic anhydride and a tertiary amine, and an organic acid, etc. In order to remove the water generated by the reaction out of the reaction system by distillation effectively, it is preferable to carry out the reaction while introducing an inert gas such as nitrogen into the reaction system.

More concretely, the reaction is carried out initially at 0° to 100° C. for several minutes to several days, followed by a later stage reaction at 40° to 300° C. (preferably 40° to 180° C.) for several tens minutes to several days. Since the imidization is accelerated in the later stage reaction, it is preferable to carry out the reaction in the pressure of acetic anhydride and pyridine.

The polyimide polymer of the present invention can be produced as follows. A dicarboxylic acid anhydride of the formula (I) is reacted with an aromatic diamine in a polar organic solvent such as N-methyl-2-pyrrolidone, dimethylacetamide, or the like at 0° to 100° C., preferably 0° C. to 60° C. to give a polyamide-acid of the formula:

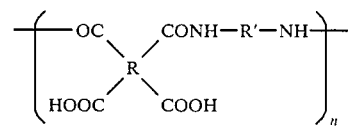

wherein R is a tetracarboxylic acid anhydride residue; R' is a diamine residue; and n is a positive integer, followed by a conventional dehydration ring closure method.

As the dehydration ring closure method, there can be used (i) a method wherein a polymer produced is once isolated, followed by ring closure with heating, (ii) a method wherein the ring closure is carried out with heating in a liquid state, (iii) a method wherein the ring closure is carried out chemically using a dehydrating agent in a liquid state, etc. The method (i) is disclosed in C.E. Sruog: Macromolecular Synthesis, collective volume, vol. 1, p 295 (1977) in detail, wherein the heating is carried out at 150° to 350° C. In the method (ii), the solution is heated at 80° to 400° C., preferably 100° to 250° C. In this case, it is preferable to use together a solvent which can form an azeotropic mixture with water. Examples of such a solvent are benzene, toluene, xylene, etc. In the method (iii), the reaction is carried out in the presence of a chemical dehydrating agent at 0° to 120° C., preferably at 10° to 80° C. Examples of the chemical dehydrating agent are acid anhydrides such as acetic anhydride, propionic anhydride, butyric anhydride, benzoic anhydride, etc. In this case, it is preferable to co-use pyridine or the like to accelerate the ring closure reaction.

During the synthesis, the non-volatile component is maintained at a concentration of preferably 50% by weight or less, more preferably 15 to 30% by weight. When the concentration is too high, stirring of the reaction system becomes difficult, while when the concentration is too low, the using amount of solvent uneconomically increases. But, since the thus obtained polyimide polymer is soluble in a polar solvent, the synthesis with a high concentration can be carried out so long as the reactor is equipped with a stirring apparatus which can operate in an increased viscosity of the reaction system.

The polyimide polymer or the polyamide-acid derivative can be recovered by pouring a solvent such as a lower alcohol, e.g., methanol, ethanol, water, etc., said solvent being compatible with the above-mentioned polar organic solvent but a poor solvent for the resin, into the reaction system in large excess to give a precipitate, which is then filtered and dried.

The molecular weight of the solvent-soluble polyimide depends on the purity of the monomers used and the molar ratio of the diamine to the dicarboxylic acid anhydride of the formula (I) and one or more dicarboxylic acid anhydrides, if used, such as benzophenonetetracarboxylic acid dianhydride. For example, in the system wherein the reaction is carried out using purified monomers obtained by recrystallization with a ratio of NH$_2$/COOH=1.01 (equivalent weight ratio), it is possible to synthesize a high molecular weight polyimide having a reduced viscosity of about 2 dl/g (measured by using 100 ml of dimethylformamide dissolving 0.5 g of polyimide at 30° C., hereinafter measured by the same conditions). The ratio of -NH$_2$/-COOH of the monomers used is preferably 0.8 to 1.2 (equivalent weight ratio), more preferably 0.95 to 1.05 (equivalent weight ratio).

A part of the exo-form dicarboxylic acid anhydride of the formula (I) can be replaced by one or more dicarboxylic acid anhydrides in a limited amount as mentioned above. In order to obtain a solvent-soluble polyimide having a high molecular weight, it is preferable to use such other dicarboxylic acid anhydrides as small as possible. In the reaction of endo-HAC-S or endo-HAC-SO$_2$ with an aromatic diamine, it is impossible to obtain a solvent-soluble polyimide having a high molecular weight such as 0.3 dl/g or more in terms of the reduced viscosity.

When the reduced viscosity of the solvent-soluble polyimide is 0.3 dl/g or more, that is, the molecular weight being high, a film obtained from a varnish of such a polyimide is relatively tough. Therefore, it is preferable to use the dicarboxylic acid anhydride and the diamine so as to make the ratio of NH$_2$/COOH 0.8 to 1.2 (equivalent weight ratio) When the reduced viscosity is less than 0.3 dl/g, there is a tendency to make the resulting polyimide film brittle. Further, from the viewpoint of solvent solubility, the reduced viscosity of 3 dl/g or more is preferable.

When 2,2-bis[4-(4-aminophenoxy)phenyl]propane (hereinafter referred to as "BAPP") is used as the aromatic diamine, there can be obtained a polyimide having a low water absorption properties. The resulting polyimide has repeating units represented by the formula:

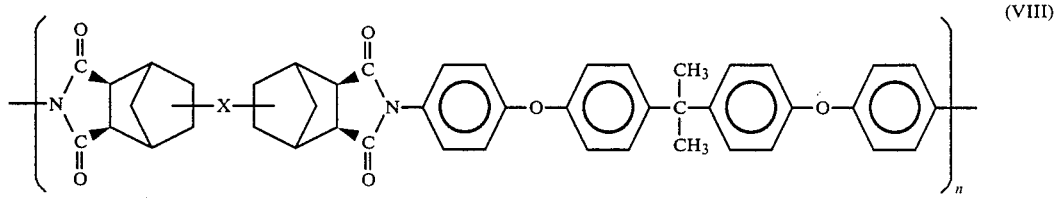

(VIII)

wherein X is S or SO$_2$; and n is a positive integer, preferably 5 or more. Particularly, a solvent-soluble polyimide having a reduced viscosity of 0.3 dl/g or more is preferable.

It is possible to use one or more aromatic diamines, aliphatic diamines, alicyclic diamines and diamonosiloxanes mentioned above in addition to BAPP (2,2-bis[4-(4-aminophenoxy)phenyl]propane) in amounts of preferably 20% by mole or less.

The reduced viscosity of the polyimide having the repeating units of the formula (VIII) can be obtained by dissolving 0.5 g of polyimide in dimethylformamide (DMF), making the resulting solution 100 ml, measuring a viscosity of the resulting solution using a Cannon-Fenske viscometer at 30° C. and calculating using the following equation:

$$\eta_{sp/c} = \frac{t - t_0}{t_0 \times 0.5}$$

wherein t$_0$ is a time in seconds of DMF; and t is a time in seconds of the sample solution.

The reaction of the dicarboxylic acid anhydride of the formula (I) with BAPP can be carried out as mentioned above.

The molecular weight of the solvent-soluble polyimide having the repeating units of the formula (VIII) depends on the purity of the monomers used and the molar ratio of BAPP to the dicarboxylic acid anhydride of the formula (I). For example, in the system wherein the reaction is carried out using purified monomers obtained by recrystallization with a ratio of NH$_2$/COOH=1.01 (equivalent weight ratio), it is possible to synthesize a high molecular weight polyimide having a reduced viscosity of about 2 dl/g. The ratio of -NH$_2$/-COOH of the monomers used is preferably 0.9 to 1.2 (equivalent weight ratio), more preferably 0.98 to 1.02 (equivalent weight ratio).

In the reaction of endo-HAC-S or endo-HAC-SO$_2$ with BAPP, it is impossible to obtain a solvent-soluble polyimide having a high molecular weight such as 0.3 dl/g or more in terms of the reduced viscosity.

When the reduced viscosity of the solvent-soluble polyimide having the repeating units of the formula (VIII) is 0.3 dl/g or more, a film obtained from a varnish of such a polyimide is relatively tough and the water absorption is 4% or less. Therefore, it is preferable to use the dicarboxylic acid and BAPP so as to make the ratio $NH_2/COOH$ 0.9 to 1.2 (equivalent weight ratio). When the reduced viscosity is less than 0.3 dl/g, there is a tendency to make the resulting polyimide film brittle.

The solvent-soluble polyimide of the present invention can be used for forming films for various uses.

The solvent-soluble polyimide of the present invention can also be used for forming an orientation controlling film in color or non-color liquid crystal display devices.

The orientation controlling film can be prepared as follows. First a solution of polyimide or polyamide-acid having a concentration of preferably 0.01 to 10% by weight, more preferably 0.1 to 5% by weight, is prepared. In this case, it is possible to use the reaction solution obtained as mentioned above with dilution, or to dissolve the recovered polymer as mentioned above in an organic solvent. If necessary, one or more other resins may be added thereto.

As the solvent, there can be used dimethyl sulfoxide, dimethylformamide, dimethylacetamide, N-methyl-2-pyrrolidone, dimethyl imidazolinone, cyclohexanone, etc., alone or as a mixture thereof.

The thus obtained solution is coated on a substrate having transparent electrodes thereon by a conventional method such as a spin coating method, a roll coating method, a spray coating method, a dip method, or the like followed by drying with heating. It is possible to use a relatively low heating temperature such as 100° to 200° C. When a polyamide-acid derivative solution is coated, it is necessary to further heat at 170° to 200° C. for 10 to 30 minutes to complete the imidization. In the case of the polyimide of the present invention, it is possible to use a lower imidization temperature than a known aromatic polyamide, and a temperature of 100° to 200° C. is sufficient.

After forming a polyimide film of 100 to 30,000 Å thick, preferably 500 to 2000 Å thick, on the substrate, the polyimide film is subjected to a rubbing treatment to give an orientation controlling film.

A pair of thus obtained substrates having said electrodes and orientation films are placed in opposition to each other so that their respective orientation films will face each other, and then they are bonded to each other in a way to form a predetermined space therebetween by interposing a spacer between them or by other means. A conventional liquid crystal composition is poured into said space and then the pouring opening is closed. In this way, a liquid crystal display device of this invention can be obtained.

The liquid crystal display device of the present invention is not only good in orientation properties of liquid crystals but also good in moisture resistance. Therefore, as the substrate material, there can be used glass, a plate of metal such as silicon, aluminum, nickel, or the like, a film or sheet made from an epoxy resin, an acrylate resin, polyethylene terephthalate, etc. Such a substrate has a transparent electroconductive film such as indium oxide film thereon. It is also possible to use conventionally used films or sheets (having a transparent electroconductive film thereon) so long as they are insoluble in or treated so as not to be dissolved in liquid crystals.

This invention is illustrated by way of the following Examples, in which all percents are by weight unless otherwise specified.

EXAMPLE 1

| Ingredients | Grams | Mole |
|---|---|---|
| Exo-HAC-SO$_2$ | 396 | 1.0 |
| 4,4'-Diaminodiphenyl ether (DDE) | 202 | 1.01 |
| N-Methyl-2-pyrrolidone (NMP) | 2390 | (Non-volatile component (NV):20%) |
| Aqueous solution of phosphoric acid (phosphoric acid content 85%) | 5.76 | 0.05 |

The above-mentioned ingredients were placed in a four-necked flask equipped with a thermometer, a stirrer, a nitrogen introducing pipe, a water content analyzer, and a condenser, and heated to 80° C. with stirring while introducing a nitrogen gas. A polyamide-acid was prepared by reacting at 80° C. for 4 hours. The temperature was raised gradually and dehydration ring closure reaction was carried out at 180° C. for 6 hours, while removing the water generated out of the system by distillation. The temperature was further raised to 205° C. and the reaction was carried out in a temperature range of 205° to 208° C., while removing NMP and remaining condensation water by distillation. The end point of the reaction was controlled by the amount of water distilled out and HPLC (high performance liquid chromatography) to obtain a polyimide resin having a reduced viscosity of 2.02 dl/g.

The obtained polyimide resin solution was diluted with NMP to give a varnish having a resin content of about 15%. The varnish was coated on a smooth glass plate in 80 μm thick and baked in a hot air drying device at 250° C. for 30 minutes.

The resulting film was evaluated variously. The results are shown in Table 1.

EXAMPLE 2

| Ingredients | Grams | Mole |
|---|---|---|
| Exo-HAC-SO$_2$ | 396 | 1.00 |
| 4,4'-Diaminodiphenylmethane | 199.98 | 1.01 |
| NMP | 2384 | (NV: 20%) |
| Aqueous solution of phosphoric acid (85%) | 5.76 | 0.05 |

Using the above-mentioned ingredients, a polyimide resin having a reduced viscosity of 1.20 dl/g was obtained in the same manner as described in Example 1. A film was prepared in the same manner as described in Example 1 and evaluated. The results are shown in Table 1.

| Ingredients | Grams | Mole |
|---|---|---|
| Exo-HAC-SO$_2$ | 396 | 1.00 |
| m-Phenylenediamine (m-PDA) | 109.08 | 1.01 |
| NMP | 2020 | (NV: 20%) |
| Aqueous solution of phosphoric acid (85%) | 5.76 | 0.05 |

Using the above-mentioned ingredients, a polyimide resin having a reduced viscosity of 0.6 dl/g was obtained in the same manner as described in Example 1. A film was prepared in the same manner as described in Example 1 and evaluated. The results are shown in Table 1.

EXAMPLE 4

| Ingredients | Grams | Mole |
|---|---|---|
| Exo-HAC-SO$_2$ | 396 | 1.00 |
| 2,2-Bis[4-(4-aminophenoxy)-phenyl]propane (BAPP) | 418.14 | 1.01 |
| NMP | 3256 | (NV: 20%) |
| Aqueous solution of phosphoric acid (85%) | 5.76 | 0.05 |

Using the above-mentioned ingredients, a polyimide resin having a reduced viscosity of 1.4 dl/g was obtained in the same manner as described in Example 1. A film was prepared in the same manner as described in Example 1 and evaluated. The results are shown in Table 1.

EXAMPLE 5

| Ingredients | Grams | Mole |
|---|---|---|
| Exo-HAC-SO$_2$ | 277.2 | 0.7 |
| Pyromellitic anhydride | 65.4 | 0.3 |
| DDE | 202 | 1.01 |
| NMP | 2178 | (NV: 20%) |
| Aqueous solution of phosphoric acid (85%) | 5.76 | 0.05 |

Using the above-mentioned ingredients, a polyimide resin having a reduced viscosity of 1.87 dl/g was obtained in the same manner as described in Example 1. This varnish had a higher viscosity than that of Example 1. A film was prepared in the same manner as described in Example 1 and evaluated. The results are shown in Table 1.

EXAMPLE 6

| Ingredients | Grams | Mole |
|---|---|---|
| Exo-HAC-SO$_2$ | 198 | 0.5 |
| Benzophenonetetracarboxylic dianhydride (BTDA) | 161 | 0.5 |
| DDE | 202 | 1.01 |
| NMP | 2244 | (NV: 20%) |
| Aqueous solution of phosphoric acid (85%) | 5.76 | 0.05 |

Using the above-mentioned ingredients, a polyimide resin having a reduced viscosity of 1.60 dl/g was obtained in the same manner as described in Example 1. Infrared absorption spectrum of the obtained polyimide resin is shown in FIG. 1. A film was prepared in the same manner as described in Example and evaluated. The results are shown in Table 1.

EXAMPLE 7

| Ingredients | Grams | Mole |
|---|---|---|
| Exo-HAC-SO$_2$ | 396 | 1.0 |
| BAPP | 369 | 0.9 |
| 1,3-Bis(aminopropyl)tetramethyldisiloxane | 24.8 | 0.1 |
| NMP | 3159 | (NV: 20%) |
| Aqueous solution of phosphoric acid (85%) | 5.76 | 0.05 |

Using the above-mentioned ingredients, a polyimide resin having a reduced viscosity of 0.67 dl/g was obtained in the same manner as described in Example 1. A film was prepared in the same manner as described in Example 1 and evaluated. The results are shown in Table 1.

EXAMPLE 8

| Ingredients | Grams | Mole |
|---|---|---|
| Exo-HAC-SO$_2$ | 277.2 | 0.7 |
| Benzophenonetetracarboxylic dianhydride (BTDA) | 96.6 | 0.3 |
| DDE | 202 | 1.01 |
| NMP | 2303 | (NV: 20%) |
| Aqueous solution of phosphoric acid (85%) | 5.76 | 0.05 |

Using the above-mentioned ingredients, a polyimide resin having a reduced viscosity of 1.8 dl/g was obtained in the same manner as described in Example 1. A film was prepared in the same manner as described in Example 1 and evaluated. The results are shown in Table 1.

EXAMPLE 9

| Ingredients | Grams | Mole |
|---|---|---|
| Exo-HAC-SO$_2$ | 198 | 0.5 |
| Endo-HAC-SO$_2$ | 79.2 | 0.2 |
| BTDA | 96.6 | 0.3 |
| DDE | 202 | 1.01 |
| NMP | 1742 | (NV: 20%) |
| Aqueous solution of phosphoric acid (85%) | 5.76 | 0.05 |

Using the above-mentioned ingredients, a polyimide resin having a reduced viscosity of 0.60 dl/g was obtained in the same manner as described in Example 1. A film was prepared in the same manner as described in Example 1 and evaluated. The results are shown in Table 1.

EXAMPLE 10

| Ingredients | Grams | Mole |
|---|---|---|
| Exo-HAC-SO$_2$ | 277.2 | 0.7 |
| Pyromellitic dianhydride (PMDA) | 21.8 | 0.1 |
| BTDA | 96.6 | 0.2 |
| DDE | 102 | 0.51 |
| BAPP | 205 | 0.50 |
| NMP | 2810 | (NV: 20%) |
| Aqueous solution of phosphoric acid (85%) | 5.76 | 0.05 |

Using the above-mentioned ingredients, a polyimide resin having a reduced viscosity of 1.0 dl/g was obtained in the same manner as described in Example 1. A film was prepared in the same manner as described in Example 1 and evaluated. The results are shown in Table 1.

EXAMPLE 11

| Ingredients | Grams | Mole |
|---|---|---|
| Exo-HAC-SO$_2$ | 277.2 | 0.7 |
| BTDA | 96.6 | 0.3 |
| DDE | 142 | 0.71 |
| BAPP | 123 | 0.3 |
| NMP | 2555 | (NV: 20%) |
| Aqueous solution of phosphoric acid (85%) | 5.76 | 0.05 |

Using the above-mentioned ingredients, a polyimide resin having a reduced viscosity of 0.88 dl/g was obtained in the same manner as described in Example 1. A film was prepared in the same manner as described in Example 1 and evaluated. The results are shown in Table 1.

EXAMPLE 12

| Ingredients | Grams | Mole |
| --- | --- | --- |
| Exo-HAC-SO$_2$ | 277.2 | 0.7 |
| BTDA | 96.6 | 0.3 |
| DDE | 142 | 0.71 |
| 4,4'-Diaminodiphenylmethane (DAM) | 59.4 | 0.3 |
| NMP | 2300 | (NV: 20%) |
| Aqueous solution of phosphoric acid (85%) | 5.76 | 0.05 |

Using the above-mentioned ingredients, a polyimide resin having a reduced viscosity of 0.86 dl/g was obtained in the same manner as described in Example 1. A film was prepared in the same manner as described in Example 1 and evaluated. The results are shown in Table 1.

EXAMPLE 13

| Ingredients | Grams | Mole |
| --- | --- | --- |
| Exo-HAC-SO$_2$ | 277.2 | 0.7 |
| BTDA | 96.6 | 0.3 |
| DDE | 142 | 0.71 |
| BAPP | 82 | 0.20 |
| 1,3-Bis(aminopropyl)tetramexylsiloxane | 24.8 | 0.10 |
| NMP | 2490 | (NV: 20%) |
| Aqueous solution of phosphoric acid (85%) | 5.76 | 0.05 |

Using the above-mentioned ingredients, a polyimide resin having a reduced viscosity of 0.6 dl/g was obtained in the same manner as described in Example 1. A film was prepared in the same manner as described in Example 1 and evaluated. The results are shown in Table 1.

EXAMPLE 14

| Ingredients | Grams | Mole |
| --- | --- | --- |
| Exo-HAC-SO$_2$ | 277.2 | 0.7 |
| BTDA | 96.6 | 0.3 |
| DDE | 142 | 0.71 |
| m-Phenylenediamine | 32.4 | 0.30 |
| NMP | 2193 | (NV: 20%) |
| Aqueous solution of phosphoric acid (85%) | 5.76 | 0.05 |

Using the above-mentioned ingredients, a polyimide resin having a reduced viscosity of 0.60 dl/g was obtained in the same manner as described in Example 1. A film was prepared in the same manner as described in Example 1 and evaluated. The results are shown in Table 1.

EXAMPLE 15

| Ingredients | Grams | Mole |
| --- | --- | --- |
| Exo-HAC-SO$_2$ | 396 | 1.0 |
| Diaminodiphenyl ether (DDE) | 40 | 0.2 |
| BAPP | 328 | 0.8 |
| NMP | 3056 | (NV: 20%) |
| Aqueous solution of phosphoric acid (85%) | 5.76 | 0.05 |

Using the above-mentioned ingredients, a polyimide having a reduced viscosity of 0.80 dl/g was obtained in the same manner as described in Example 1. A film was prepared in the same manner as described in Example 1 and evaluated. The results are shown in Table 1.

EXAMPLE 16

| Ingredients | Grams | Mole |
| --- | --- | --- |
| Exo-HAC-SO$_2$ | 198 | 0.5 |
| BTDA | 161 | 0.5 |
| BAPP | 418 | 1.01 |
| NMP | 3108 | (NV: 20%) |
| Aqueous solution of phosphoric acid (85%) | 5.76 | 0.05 |

Using the above-mentioned ingredients, a polyimide having a reduced viscosity of 0.60 dl/g was obtained in the same manner as described in Example 1. A film was prepared in the same manner as described in Example 1 and evaluated. The results are shown in Table 1.

COMPARATIVE EXAMPLE 1

| Ingredients | Grams | Mole |
| --- | --- | --- |
| Pyromellitic anhydride | 218 | 1.0 |
| DDE | 202 | 1.01 |
| NMP | 1120 | (NV: 20%) |
| Aqueous solution of phosphoric acid (85%) | 5.76 | 0.05 |

Using the above-mentioned ingredients, the reaction was carried out in the same manner as described in Example 1. A polyamide-acid produced was dissolved in the solvent. But when the dehydration ring closure reaction was carried out at elevated temperatures, an insoluble material was deposited and then became a paste state. Since stirring became difficult, the reaction was stopped.

COMPARATIVE EXAMPLE 2

| Ingredients | Grams | Mole |
| --- | --- | --- |
| BTDA | 322 | 1.0 |
| DDE | 202 | 1.01 |
| NMP | 2096 | (NV: 20%) |
| Aqueous solution of phosphoric acid (85%) | 5.76 | 0.05 |

Using the above-mentioned ingredients, the reaction was carried out in the same manner as described in Example 1. In the state of a polyamide-acid, the reaction solution was a viscous solution. But with the progress of dehydration ring closure while increasing the temperature, an insoluble agar-like material was produced. Since gelation took place, the reaction was stopped.

COMPARATIVE EXAMPLE 3

| Ingredients | Grams | Mole |
|---|---|---|
| Endo-HAC-SO$_2$ | 396 | 1.0 |
| DDE | 202 | 1.01 |
| NMP | 2390 | (NV: 20%) |
| Aqueous solution of phosphoric acid (85%) | 5.76 | 0.05 |

Using the above-mentioned ingredients, the reaction was carried out in the same manner as described in Example 1, but no rise in viscosity was observed. The heat treatment at high temperatures was further continued, but no rise in viscosity took place. It was confirmed by infrared absorption spectrum that the imidization took place. The resulting polyimide had a reduced viscosity of 0.25 dl/g and was not able to form a film. Using a piece of the resin, properties were evaluated and listed in Table 1.

COMPARATIVE EXAMPLE 4

| Ingredients | Grams | Mole |
|---|---|---|
| Exo-HAC-SO$_2$ | 150.4 | 0.4 |
| Endo-HAC-SO$_2$ | 237.6 | 0.6 |
| DDE | 202 | 1.01 |
| NMP | 2390 | (NV: 20%) |
| Aqueous solution of phosphoric acid (85%) | 5.76 | 0.05 |

Using the above-mentioned ingredients, a polyimide was prepared in the same manner as described in Example 1. But the resulting polyimide had a reduced viscosity of as low as 0.28 dl/g. A film was tried to be prepared in the same manner as described in Example 1, but only scale-like small films were obtained. The films were very brittle.

COMPARATIVE EXAMPLE 5

| Ingredients | Grams | Mole |
|---|---|---|
| Exo-HAC-SO$_2$ | 118.8 | 0.3 |
| BTDA | 225.4 | 0.7 |
| DDE | 202 | 1.01 |
| NMP | 2185 | (NV: 20%) |
| Aqueous solution of phosphoric acid (85%) | 5.76 | 0.05 |

Using the above-mentioned ingredients, the reaction was carried out in the same manner as described in Example 1. In the state of polyamide-acid, the reaction solution was viscous. With the progress of dehydration ring closure while increasing the temperature, an insoluble agar-like material was produced. Since gelation took place, the reaction was stopped.

TABLE 1

| | Examples | | | | | | | | | | |
|---|---|---|---|---|---|---|---|---|---|---|---|
| | 1 | 2 | 3 | 4 | 5 | 6 | 7 | 8 | 9 | 10 | 11 |
| Exo-HAC-SO$_2$ | 1.0 | 1.0 | 1.0 | 1.0 | 0.7 | 0.5 | 1.0 | 0.7 | 0.5 | 0.7 | 0.7 |
| Endo-HAC-SO$_2$ | | | | | | | | | 0.2 | | |
| Pyromellitic dianhydride | | | | | 0.3 | | | | | 0.1 | |
| BTDA | | | | | | 0.5 | | 0.3 | 0.3 | 0.2 | 0.3 |
| DDE | 1.01 | | | | 1.01 | 1.01 | | 1.01 | 1.01 | 0.51 | 0.7 |
| 4,4'-Diamidiphenyl-methane | | 1.01 | | | | | | | | | |
| m-Phenylenediamine | | | 1.01 | | | | | | | | |
| BAPP | | | | 1.01 | | | 0.9 | | | 0.5 | 0.3 |
| 1,3-Bis(aminopropyl)-tetramethyldisiloxane | | | | | | | 0.1 | | | | |
| Solubility | | | | | | | | | | | |
| Film properties | | | x | | | | | | | | |
| Coloring of film | Pale yellow | Brown | Yellow | | | | | | Yellow | | |
| Transmittance of film (nm) | 425 | | | | | | 550 or more | | | | |
| Reduced viscosity (dl/g) | 2.02 | 1.2 | 0.6 | 1.4 | 1.87 | 1.6 | 0.67 | 1.8 | 0.6 | 1.0 | 0.88 |
| Tg (°C.) | 358 | 357 | 260 | 311 | 344 | 325 | 296 | 340 | 303 | 340 | 320 |
| Water absorption (%) | 8.0 | 6.0 | 6.2 | 2.8 | 6.0 | 2.5 | 2.3 | 3.0 | 4.0 | 2.3 | 2.0 |

| | Examples | | | | | Comparative Examples | | | | |
|---|---|---|---|---|---|---|---|---|---|---|
| | 12 | 13 | 14 | 15 | 16 | 1 | 2 | 3 | 4 | 5 |
| Exo-HAC-SO$_2$ | 0.7 | 0.7 | 0.7 | 1.0 | 0.5 | | | | 0.4 | 0.3 |
| Endo-HAC-SO$_2$ | | | | | | | | 1.0 | 0.6 | |
| Pyromellitic dianhydride | | | | | | 1.0 | | | | |
| BTDA | 0.3 | 0.3 | 0.3 | | 0.51 | | 1.0 | | | 0.7 |
| DDE | 0.7 | 0.7 | 0.7 | 0.2 | | 1.01 | 1.01 | 1.01 | 1.01 | 1.01 |
| 4,4'-Diamidiphenyl-methane | 0.3 | | | | | | | | | |
| m-Phenylenediamine | | | 0.3 | | | | | | | |
| BAPP | | 0.2 | | 0.8 | | | | | | |
| 1,3-Bis(aminopropyl)-tetramethyldisiloxane | | 0.1 | | | | | | | | |
| Solubility | | | | | | X | X | | | X |
| Film properties | | | | | | — | — | X | X | — |
| Coloring of film | Dark yellow | Yellow | Yellowish brown | Yellow | | — | — | Yellow | — | |
| Transmittance of film | | 550 or more | | | | — | — | ≧500 | — | |

TABLE 1-continued

| (nm) | | | | | | | | | | |
|---|---|---|---|---|---|---|---|---|---|---|
| Reduced viscosity (dl/g) | 0.86 | 0.60 | 0.60 | 0.8 | 0.60 | — | — | 0.25 | 0.28 | — |
| Tg (°C.) | 340 | 305 | 325 | 320 | 320 | — | — | 268 | 280 | — |
| Water absorption (%) | 2.8 | 1.6 | 3.5 | 3.5 | 1.8 | — | — | 4.0 | 2.4 | — |

In Table 1, various properties were measured as follows.

Reduced viscosity:

Into 500 ml of acetone stirred at a high speed, a 10% polyimide varnish was gradually dropped to deposit a resin. The deposit resin was filtered and refluxed in 300 ml acetone for 3 hours to remove the solvent, followed by drying at 150° C. for 2 hours in a reduced-pressure drier to give powdery polyimide resin. Measuring conditions were as follows:

| Sample concentration: | 0.5 g/dl |
|---|---|
| Measuring solvent: | dimethylformamide |
| Measuring temperature: | 30° C. |
| Viscometer: | Cannon-Fenske viscometer |
| Reduced viscosity ($\eta$sp/c): | $\eta sp/c = \dfrac{t - t_0}{t_0 \times 0.5}$ | where $t_0$: DMF in seconds
t: Sample solution in seconds

Glass transition temperature (Tg):

Tg of a film was measured by using a thermophysical tester (mfd. by Perkin Elmer Co.) under the following conditions:

| Measuring conditions: | a tension method |
|---|---|
| Temperature rise rate: | 5° C./min |
| Load: | 5 g |
| Sample: | 2 mm wide |
| Span: | 10 mm |

Transmittance of film:

Using a film of 50 μm thick, transmittance was measured using a Hitachi visible UV spectrophotometer in the wavelength range of 900 to 400 nm. The transmittance was evaluated at a wavelength beginning to reduce the transmittance.

Solubility:

A polyimide film in an amount of 10 g was placed in 90 ml of dimethylacetamide (DMA), dimethylformamide (DMF), N-methylpyrrolidone (NMP) or methyl sulfoxide (DMSO) and solubility was examined and evaluated as follows:

o: completely dissolved
x: completely not dissolved and produced a precipitate or clouding Film properties:

Film strength after baked at 250° C. for 30 minutes was tested with fingers and evaluated as follows:

o: tough
x: brittle

Coloring of film:

Coloring of film was observed by the naked eye.

Water absorption:

A film obtained in the same manner as described in Example 1 was cut in a size of 10 cm ×10 cm and dipped in purified water at 25° C. for 24 hours. The film was then taken out of the water and sandwiched with new filter papers (No. 131) to remove attached water instantly, followed by weighing and calculation using the following equation:

$$A = \dfrac{w_2 - w_1}{w_1} \times 100\ (\%)$$

wherein
A: water absorption
$w_1$ weight of the film before water absorption and after pre-dried (heated at 135° C. for 2 hours)
$w_2$ weight of the film after water absorption

EXAMPLE 17

Using the polyimide resin obtained in Example 4, various properties were measured.

Figure 2:
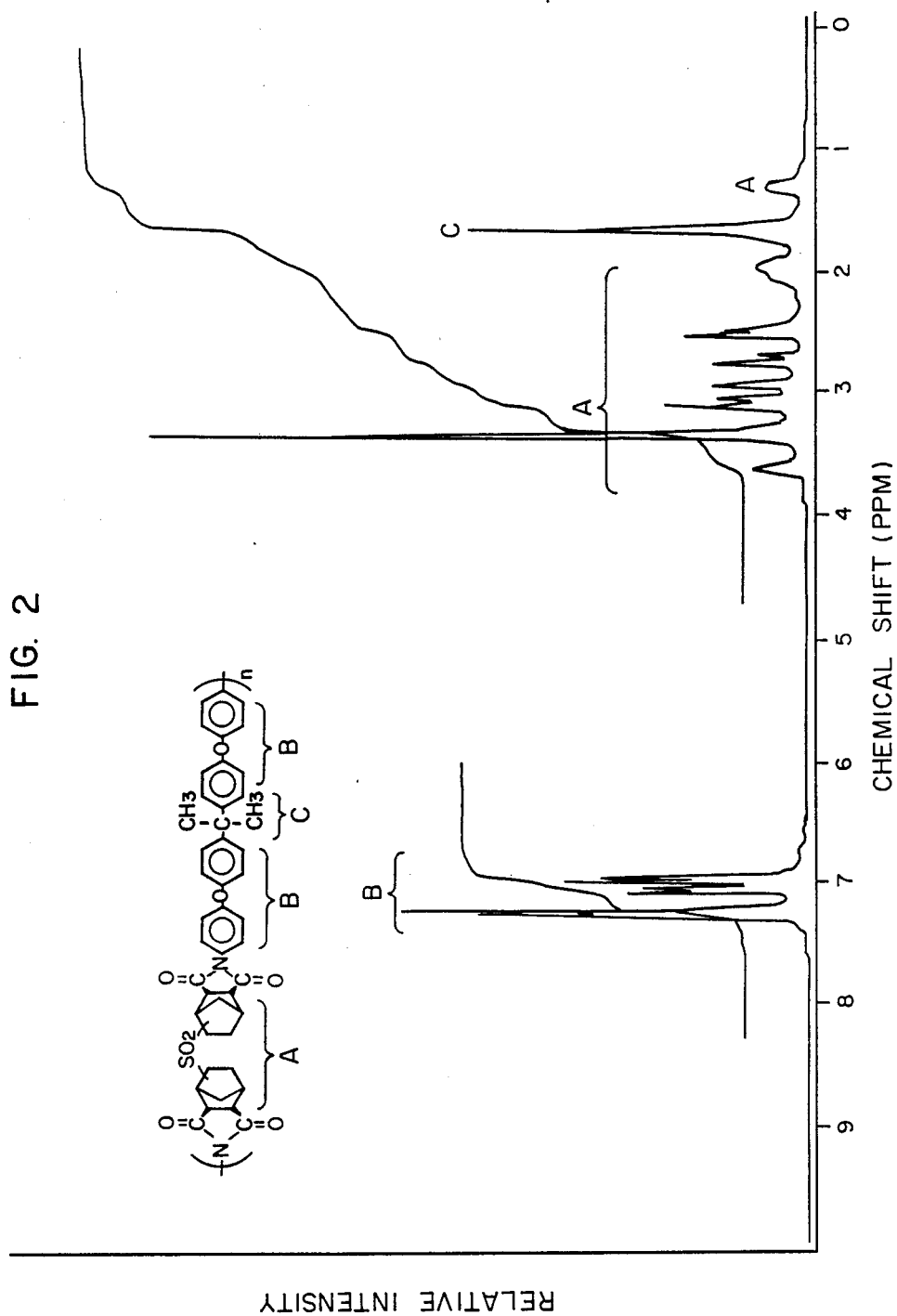
FIG. 2 is a ¹HNMR spectrum of polyimide obtained in Example 17.

FIG. 2 is an NMR spectrum of the polyimide resin obtained. In FIG. 2, the absorption A is due to the norbornene group, the absorption B is due to the diphenyl ether group, and the absorption C is due to the isopropyl group, respectively, of bis(exo-bicyclo[2,2,1-]heptane-2,3-dicarboxylic anhydride.

Figure 3:
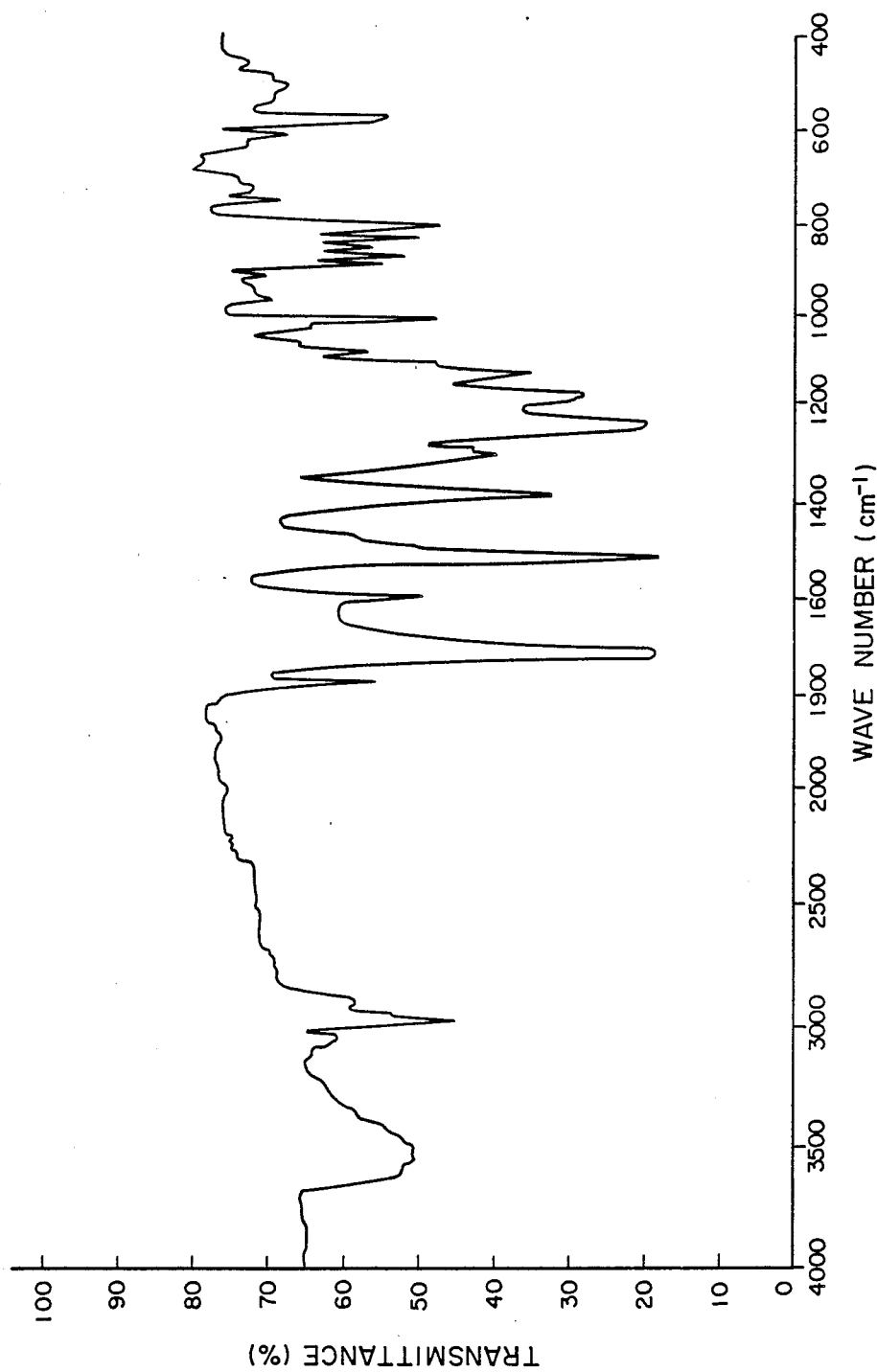
FIG. 3 is an infrared absorption spectrum of polyimide obtained in Example 17.

FIG. 3 is an infrared absorption spectrum of the polyimide resin obtained. In FIG. 3, there are shown absorptions at 1780 cm$^{-1}$ and 1720 cm$^{-1}$ due to the imido group.

Figure 4:
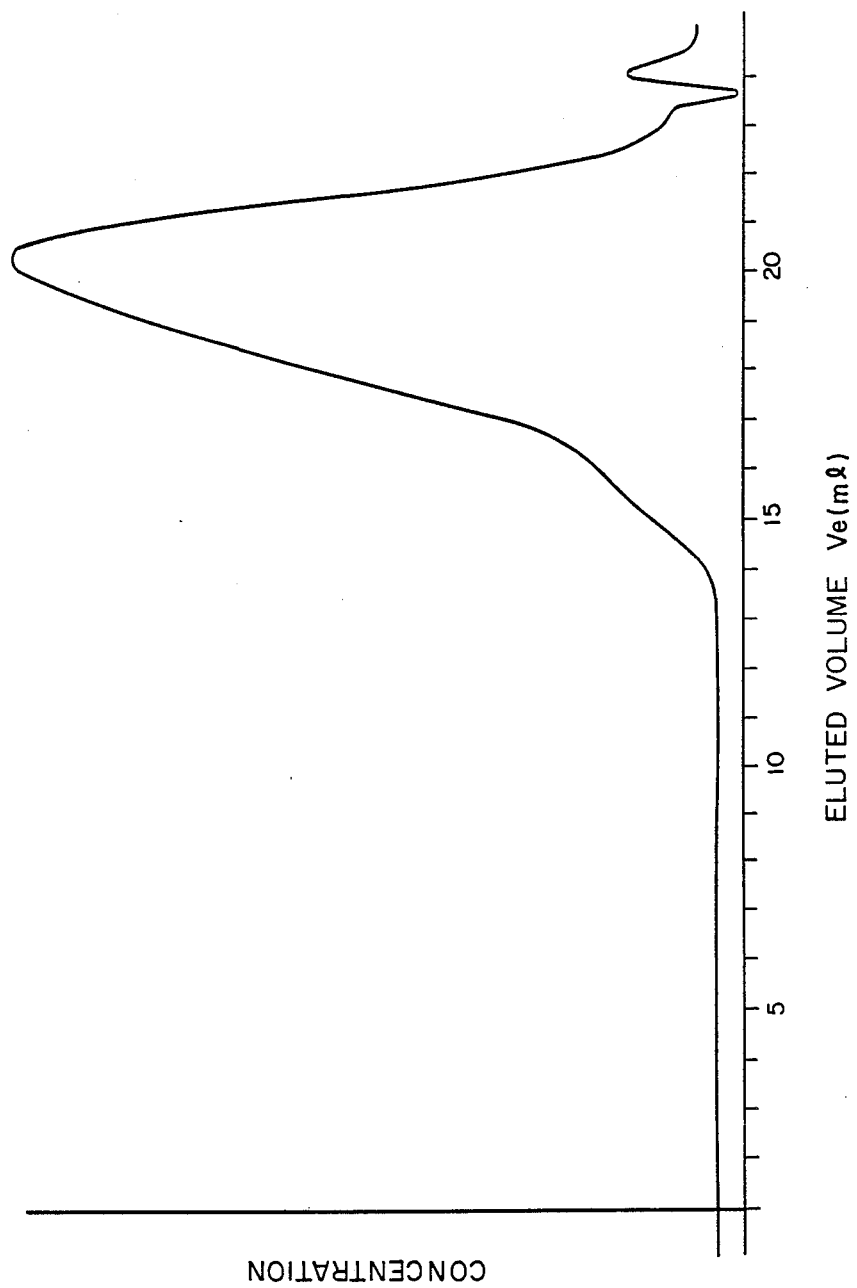
FIG. 4 is a gel permeation chromatogram of polyimide obtained in Example 17.

FIG. 4 is a GPC chromatogram of the polyimide resin obtained. The arithmetic average molecular weight converted to polystyrene was 8600. Thus, the value of n in the formula (VIII) is about 11.

Measuring conditions of GPP were as follows:

| Column: | Gelpack S-300 MDT-5 × 2 |  |
|---|---|---|
|  | (mfd. by Hitachi Chemical Co., Ltd.) | |
| Eluent: | DMF/THF = 1/1 (vol.) | |
|  | Buffer: LiBr H$_2$O | 0.03 mole/l |
|  | H$_3$PO$_4$ | 0.06 mole/l |
| Flow rate: | 1 ml/min | |
| Detector: | UV 270 nm | |

EXAMPLE 18

| Ingredients | Grams | Mole |
|---|---|---|
| Exo-HAC-S | 364 | 1.00 |
| BAPP | 418 | 1.01 |
| NMP | 3128 | (NV: 20%) |
| Aqueous solution of phosphoric acid (85%) | 5.76 | 0.05 |

Using the above-mentioned ingredients, a polyimide having a reduced viscosity of 2.0 dl/g was obtained in the same manner as described in Example 1. A film was prepared in the same manner as described in Example 1 and evaluated. The results are shown in Table 2.

Figure 5:
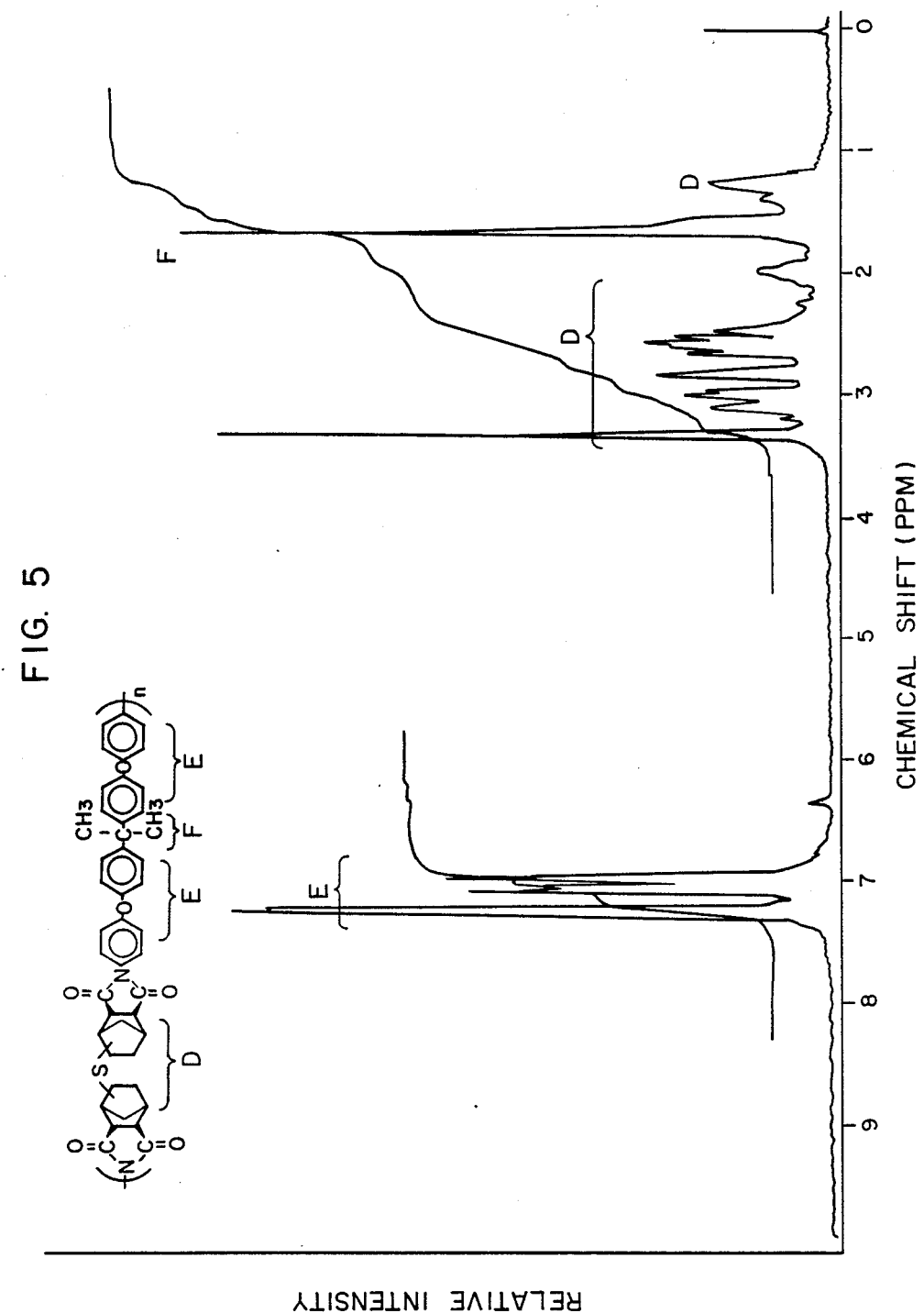
FIG. 5 is a ¹HNMR spectrum of polyimide obtained in Example 18.

FIG. 5 is an NMR spectrum of the polyimide resin obtained. In FIG. 5, the absorption D is due to the norbornene group, the absorption E is due to the diphenyl ether group and the absorption F is due to the diphenyl ether group, respectively, of bis(exobicyclo[2,2,1]heptane-2,3-dicarboxylic acid anhydride.

Figure 6:
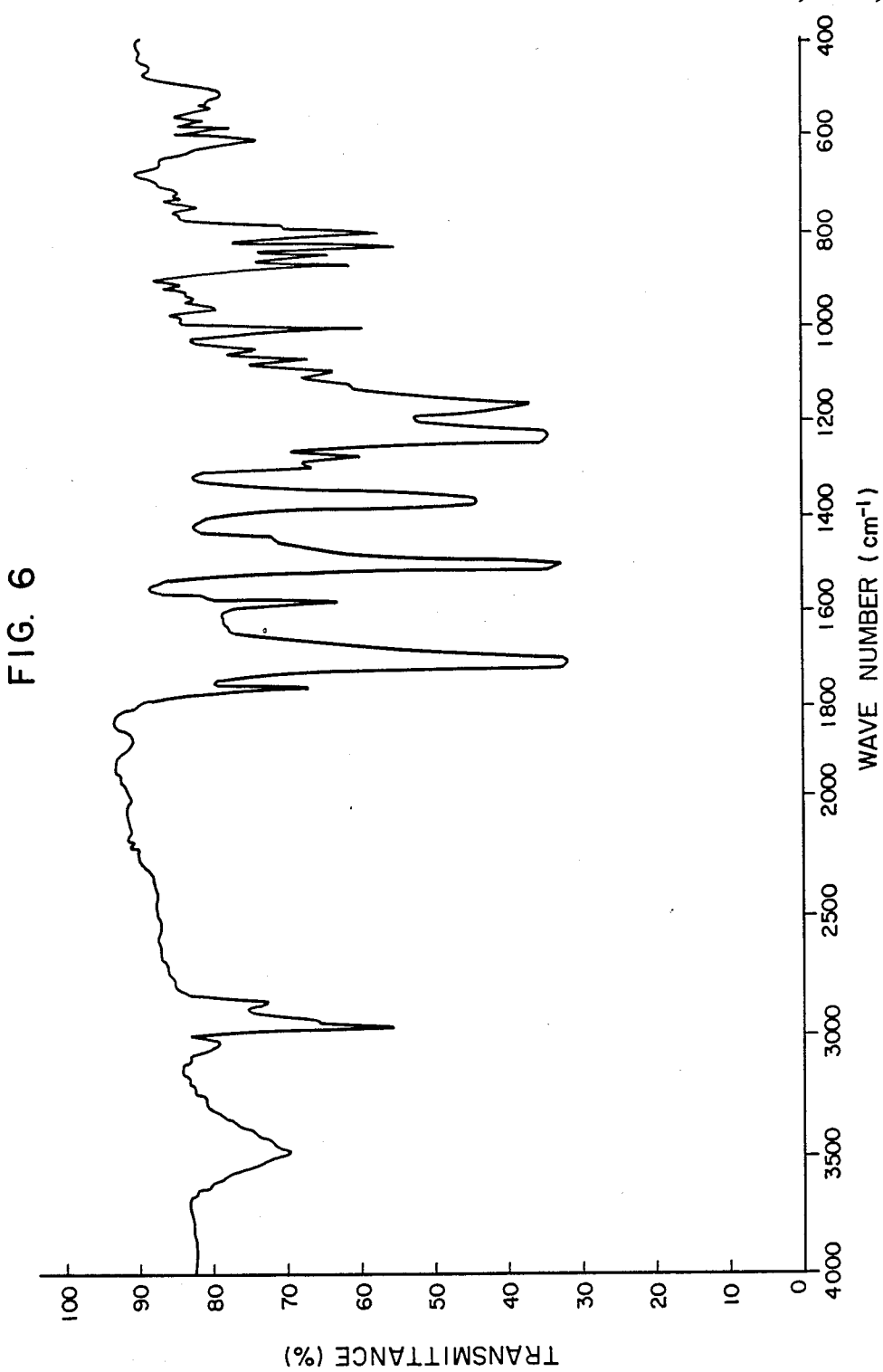
FIG. 6 is an infrared absorption spectrum of polyimide obtained in Example 18.

FIG. 6 is an infrared absorption spectrum of the polyimide resin obtained. In FIG. 6, there are shown absorptions at 1780 cm$^{-1}$ and 1720 cm$^{-1}$ due to the imido group.

Figure 7:
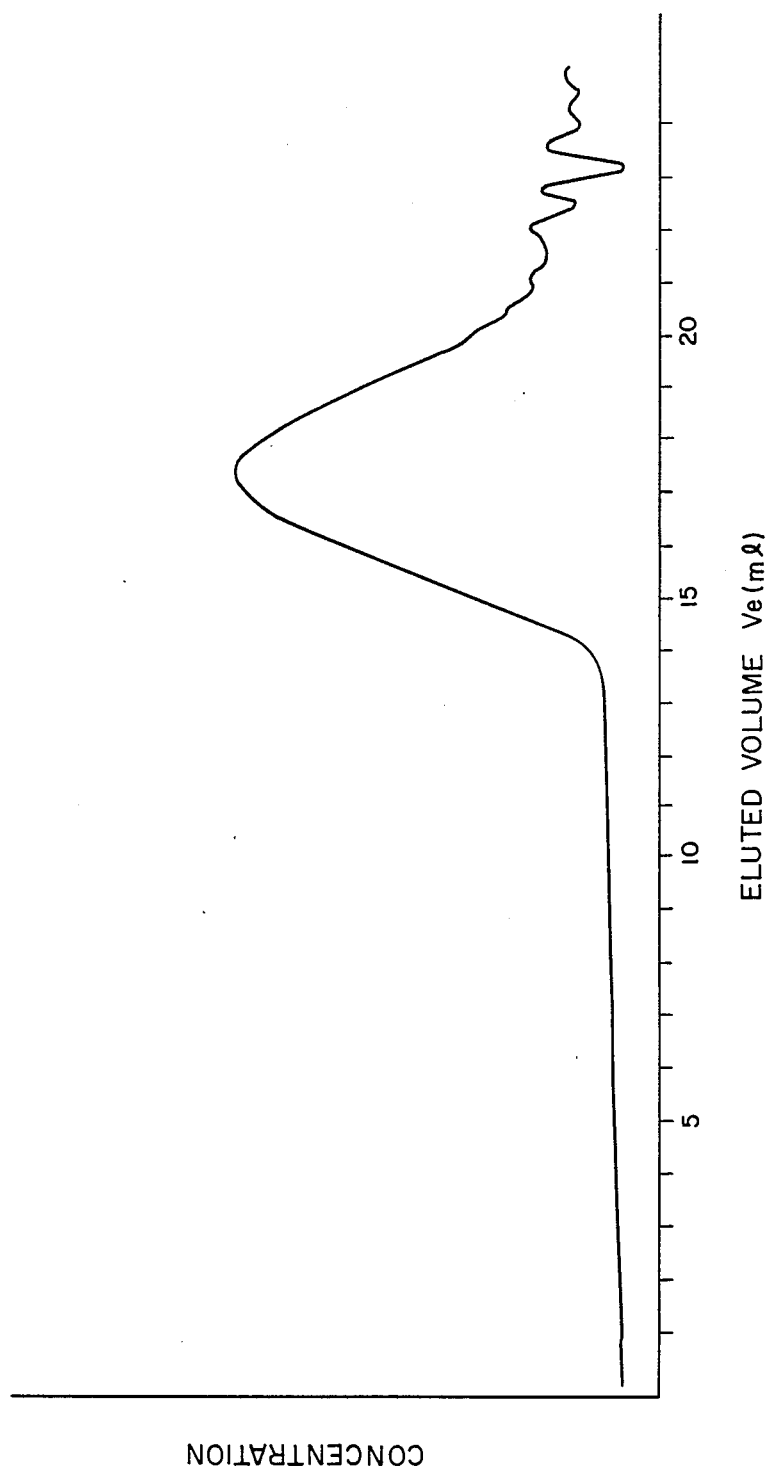
FIG. 7 is a gel permeation chromatogram (GPC) of polyimide obtained in Example 18.

FIG. 7 is a GPC chromatogram of the polyimide resin obtained. The arithmetic average molecular weight was 19000 converted to polystyrene. Thus, the value of n in the formula (VIII) is about 24. The measuring conditions for GPC were the same as those used in Example 17.

COMPARATIVE EXAMPLE 6

| Ingredients | Grams | Mole |
|---|---|---|
| Endo-HAC-SO$_2$ | 396 | 1.0 |
| BAPP | 202 | 1.01 |
| NMP | 2390 | (NV: 20%) |
| Aqueous solution of phosphoric acid (85%) | 5.76 | 0.05 |

Using the above-mentioned ingredients, the reaction was carried out in the same manner as described in Example 1, but no rise in viscosity was observed. The heat treatment at high temperatures was further continued, but no rise in viscosity took place. It was confirmed by infrared absorption spectrum that the imidization took place. The resulting polyimide had a reduced viscosity of 0.24 dl/g and was not able to form a film. Using a piece of the resin, properties were evaluated and listed in Table 2.

COMPARATIVE EXAMPLE 7

| Ingredients | Grams | Mole |
|---|---|---|
| Endo-HAC-S | 364 | 1.00 |
| BAPP | 418 | 1.01 |
| NMP | 3128 | (NV: 20%) |
| Aqueous solution of phosphoric acid (85%) | 5.76 | 0.05 |

Using the above-mentioned ingredients, the reaction was carried out in the same manner as described in Example 1, but no rise in viscosity was observed. The heat treatment at high temperatures was further continued, but no rise in viscosity took place. It was conformed by infrared absorption spectrum that the imidization took place. The resulting polyimide had a reduced viscosity of 0.20 dl/g and was not able to form a film. Using a piece of the resin, properties were evaluated and listed in Table 2.

TABLE 2

| | Examples | | Comparative Examples | |
|---|---|---|---|---|
| | 17 | 18 | 6 | 7 |
| Reduced viscos viscosity (dl/g) | 1.4 | 2.0 | 0.24 | 0.20 |
| Tg (°C.) | 311 | 318 | 260 | 240 |
| Transmittance of film (nm) | ≧550 | ≧550 | ≧550 | ≧550 |
| Solubility | o | o | o | o |
| Film properties | o | o | x | x |
| Coloring of film | yellow | yellow | yellow | yellow |
| Water absorption (%) | 2.8 | 2.5 | — | — |

EXAMPLE 19

In a four-necked flask equipped with a thermometer, a stirrer, a nitrogen introducing pipe, a water content analyzer, and a condenser, 369 g (0.9 mole) of 2,2-bis[4-(4-aminophenoxy)phenyl]propane (BAPP), 24.8 g (0.1 mole) of 1,3-bis(3-aminopropyl)tetramethyldisiloxane and 1843 g of N-methyl-2-pyrrolidone (NMP) were placed and dissolved with stirring while introducing nitrogen. Then, 396 g (1.0 mole) of exo-HAC-SO$_2$ was added thereto with stirring at room temperature. The reaction was carried out at room temperature for 4 hours to synthesize a polyamide-acid, followed by dehydration ring closure at 180° C. for 4 hours and at 205° C. for 2 hours. The resulting reaction solution was poured into a large amount of methanol. A precipitate was filtered and dried under reduced pressure to yield a polyimide. The polyimide had a reduced viscosity of 0.97 dl/g (measured by using 0.2% solution of dimethylformamide at 30° C). Tg of the polyimide was 295° C.

A 3% varnish was prepared by dissolving 3 g of the polyimide in 97 g of N-methyl-2-pyrrolidone. The varnish was uniformly coated on a sufficiently cleaned transparent electroconductive film formed on a glass plate using a spinner at a rate of 2000 rpm, followed by drying at 150° C. for 30 minutes to evaporate the solvent to form an orientation controlling film. The resulting film was rubbed in a cirtain direction with a piece of felt to give a glass substrate having an orientation controlling film. A pair of thus prepared glass substrates were positioned in parallel facing the orientation films each other and sealed with an epoxy resin adhesive via a spacer of 10 μm thick (cured at 120° C. for 30 minutes). In the resulting space, phenylcyclohexane series liquid crystals (ZLI-1132, a trade name, mfd. by Merck & Co., Inc.) were placed and sealed.

Orientation properties of the liquid crystals were tested between a pair of polarizing plates crossed at right angles each other. The orientation properties were good. The tilt angle was 4.1°.

The orientation properties of liquid crystal display device were evaluated by the tilt angle ($\theta$), that is, an angle between a long axis direction of liquid crystal molecule and a substrate surface. To have a tilt angle of about 1.0° to 7.0° means good orientation properties. When the tilt angle becomes smaller, the response speed is fast. On the other hand, when the tilt angle becomes larger, the absolute value of contrast ratio can be made larger and disadvantages such as reverse twist, etc. can be reduced. The tilt angle and measuring method thereof are explained in detail in Journal of Applied Physics, vol. 19, No. 10. pp 2013–2014 (1980), etc.

EXAMPLE 20

The process of Example 19 was repeated except for using 466 g (0.9 mole) of 1,1,1,3,3,3-hexafluoro-2,2-bis[4-(4-aminophenoxy)phenyl]propane in place of 369 g (0.9 mole) of BAPP. The resulting polyimide had a reduced viscosity of 0.88 dl/g and a glass transition temperature (Tg) of 305° C.

An orientation controlling film of 900 Å thick was formed in the same manner as described in Example 19. A liquid crystal sealed cell was prepared in the same manner as described in Example 19. Said cell showed good orientation properties and had a tilt angle of 5.0°.

EXAMPLE 21

The reaction for producing a polyimide-acid was carried out in the same manner as described in Example 19. To the resulting polyamide-acid, NMP was added so as to make the solid content 3% in a varnish. The resulting varnish was coated on a glass plate having a transparent electroconductive film in the same manner as described in Example 19 and dried at 150° C. for 30 minutes to evaporate the solvent. Imidization was completed by further heating at 200° C. for 30 minutes to form an orientation controlling film of 800 Å thick. A liquid crystal sealed cell prepared in the same manner as described in Example 19 showed good orientation properties and had a tilt angle of 4.1°.

EXAMPLE 22

A polyimide was prepared in the same manner as described in Example 19 except for using 180 g (0.9 mole) of 4,4'-diaminodiphenyl ether in place of 369 g (0.9 mole) of BAPP. The polyimide had a reduced viscosity of 1.21 dl/g and Tg of 335° C. An orientation controlling film of 1100 Å was formed in the same manner as described in Example 19. A liquid crystal sealed cell prepared in the same manner as described in Example 19 showed good orientation properties and had a tilt angle of 4.4°.

As mentioned above, the polyimide resins obtained by the present invention are solvent-soluble, relatively excellent in transparency and good in film forming properties. Further, by using a certain amount of benzophenonetetracarboxylic dianhydride or 2,2-bis[4-(4-aminophenoxy)phenyl]propane as the aromatic diamine, the resulting polyimide is improved in moisture absorbing properties.

In addition, when the polyimide is used as an orientation controlling film, the resulting liquid crystal display device has high contrast due to its high tilt angle. Moreover, since the orientation controlling film can sufficiently be formed with heating at 200° C. or lower in the production of liquid crystal display device, it is possible to prevent the substrate from deformation and deterioration.

As mentioned above, according to the present invention, liquid crystal display devices with high contrast, light-weight and thinned form can be provided easily with low price.

The liquid crystal display devices of the present invention can contain guest-host type liquid crystals. Further, these devices can use a TFT (thin film transistor) and very good in durability without causing no problem in practical use.

What is claimed is:

1. A solvent-soluble polyimide obtained by reacting an exo-form dicarboxylic acid anhydride represented by the formula:

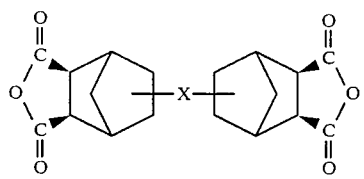

wherein X is S or $SO_2$, with an aromatic diamine in a polar solvent, followed by dehydration ring closure.

2. A polyimide according to claim 1, wherein the aromatic diamine is at least one member selected from the group consisting of:

a compound of the formula:

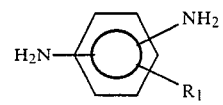

wherein $R_1$ is a hydrogen atom, a lower alkyl group, a lower alkoxy group, a chlorine atom or a bromine atom, a compound of the formula:

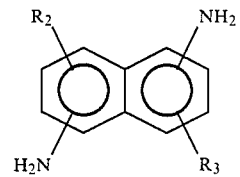

wherein $R_2$ and $R_3$ are independently a hydrogen atom, a lower alkyl group, a lower alkoxy group, a chlorine atom or a bromine atom, a compound of the formula:

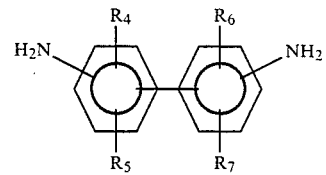

wherein $R_4$, $R_5$, $R_6$ and $R_7$ are independently a hydrogen atom, a lower alkyl group, a lower alkoxy group, a chlorine atom or a bromine atom, a compound of the formula:

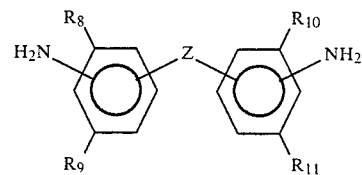

wherein Z is an alkylene group having 1 to 6 carbon atoms,

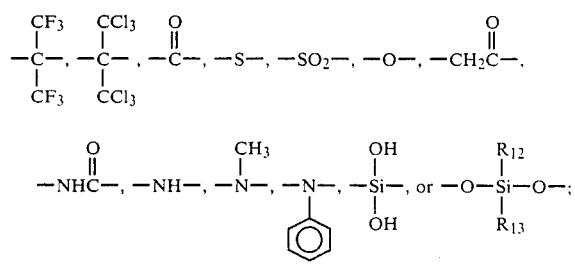

$R_8$, $R_9$, $R_{10}$ and $R_{11}$ are independently a hydrogen atom, a lower alkyl group, a lower alkoxy group, a chlorine atom or a bromine atom; and $R_{12}$ and $R_{13}$ are independently a lower alkyl group, a compound of the formula:

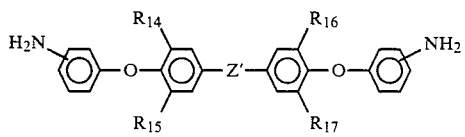

wherein Z' is an alkylene group having 1 to 6 carbon atoms,

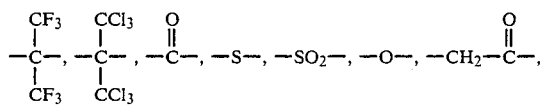

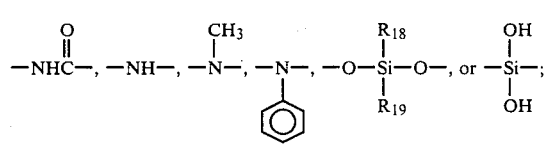

$R_{14}$, $R_{15}$, $R_{16}$ and $R_{17}$ are independently a hydrogen atom, a lower alkyl group, a lower alkoxy group, a chlorine atom or a bromine atom; and $R_{18}$ and $R_{19}$ are independently a lower alkyl group.

3. A solvent-soluble polyimide having repeating units represented by the formula:

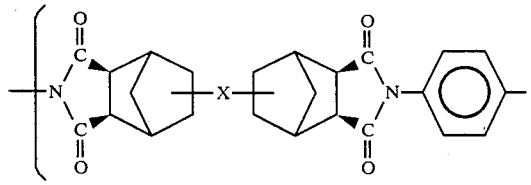

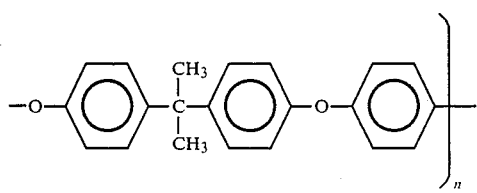

wherein X is S or $SO_2$; and n is a positive integer, and a reduced viscosity of 0.3 dl/g or more when measured at 30° C. using 100 ml of a solution of dimethylformamide dissolving 0.5 g of the polyimide.

4. A process for producing a solvent-soluble polyimide which comprises reacting an exo-form carboxylic acid anhydride represented by the formula:

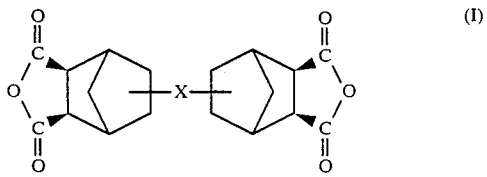

wherein X is S or $SO_2$, with an aromatic diamine in a polar solvent, followed by dehydration ring closure.

5. A process according to claim 4, wherein the reaction is continued so as to make the polyimide have a reduced viscosity of 0.3 dl/g or more when measured at 30° C. using 100 ml of a solution of dimethylformamide dissolving 0.5 g of the polyimide.

6. A process according to claim 4, wherein the exo-form carboxylic acid anhydride is used in an amount of 40 to 80% by mole together with 60 to 20% by mole of benzophenonetetracarboxylic·acid anhydride, a total acid component being 100% by mole.

7. A process according to claim 4, wherein the aromatic diamine is 2,2-bis[4-(4-aminophenoxy)phenyl]propane.

8. A process for using the solvent-soluble polyimide of claim 1 as an orientation controlling film in a liquid crystal display device.

9. A process for using the solvent-soluble polyimide of claim 3 as an orientation controlling film in a liquid crystal display device.

10. In a liquid crystal display device, the improvement wherein an orientation controlling film is made from a solvent-soluble polyimide obtained by reacting an exo-form dicarboxylic acid anhydride represented by the formula:

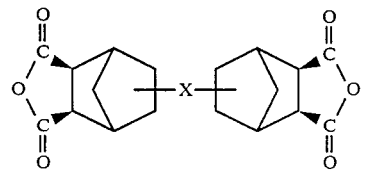

wherein X is S or $SO_2$, with an aromatic diamine in a polar solvent, followed by dehydration ring closure.

11. A polyimide according to claim 2, wherein the aromatic diamine is a mixture of at least one diamine selected from compounds of the formula (II) to (VI) and a diaminosiloxane of the formula:

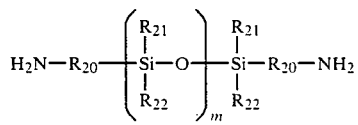

wherein $R_{20}$ is a divalent hydrocarbon; $R_{21}$ and $R_{22}$ are independently an alkyl group, a phenyl group or a phenyl group substituted with an alkyl group.

12. A process for using the solvent-soluble polyimide of claim 11 as an orientation controlling film in a liquid crystal display device.

13. A polyimide according to claim 11, wherein the diaminosiloxane is in an amount of 0.5% by mol to 50% by mol based on the total amount of the diamine.

* * * * *